US012569141B2

(12) United States Patent
Bharat et al.

(10) Patent No.: US 12,569,141 B2
(45) Date of Patent: Mar. 10, 2026

(54) SYSTEMS AND METHODS FOR LASER CATHETER TREATMENT IN A VESSEL LUMEN

(71) Applicant: KONINKLIJKE PHILIPS N.V., Eindhoven (NL)

(72) Inventors: Shyam Bharat, Arlington, MA (US); Alvin Chen, Cambridge, MA (US); Mingxin Zheng, Cambridge, MA (US); Ramon Quido Erkamp, Swampscott, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 455 days.

(21) Appl. No.: 18/009,132

(22) PCT Filed: Jun. 21, 2021

(86) PCT No.: PCT/EP2021/066741
§ 371 (c)(1),
(2) Date: Dec. 8, 2022

(87) PCT Pub. No.: WO2022/002653
PCT Pub. Date: Jan. 6, 2022

(65) Prior Publication Data
US 2023/0210379 A1      Jul. 6, 2023

Related U.S. Application Data

(60) Provisional application No. 63/045,868, filed on Jun. 30, 2020.

(51) Int. Cl.
*A61B 5/00* (2006.01)
*A61B 17/3207* (2006.01)
(Continued)

(52) U.S. Cl.
CPC ........ *A61B 5/0093* (2013.01); *A61B 17/3207* (2013.01); *A61B 18/24* (2013.01); *A61B 2018/00345* (2013.01)

(58) Field of Classification Search
CPC ... A61B 5/0093; A61B 17/3207; A61B 18/24; A61B 2018/00345; A61B 2017/00128; (Continued)

(56) References Cited

U.S. PATENT DOCUMENTS

| | | | |
|---|---|---|---|
| 6,022,309 | A | 2/2000 | Celliers |
| 6,538,739 | B1 | 3/2003 | Visuri |

(Continued)

FOREIGN PATENT DOCUMENTS

| | | |
|---|---|---|
| JP | 2019150296 A | 9/2019 |
| WO | 2019152789 A1 | 8/2019 |
| WO | 2020018722 A1 | 1/2020 |

OTHER PUBLICATIONS

International Search Report and Written Opinion Dated Sep. 24, 2021 For International Application No. PCT/EP2021/066741 Filed Jun. 21, 2021.

(Continued)

*Primary Examiner* — Ankit D Tejani
*Assistant Examiner* — Sebastian X Lukjan

(57) ABSTRACT

Systems and methods for laser catheter treatment in a vessel lumen. The method includes inserting the laser catheter within the vessel lumen to a location of a treatment area; presenting an image of the treatment area within the vessel lumen based on using an ultrasound (US) imaging system;

(Continued)

and, detecting, in real-time, a bubble cloud that is a function of the laser catheter operation (at a prescribed speed and controlling a fluence and a pulse rate) in the treatment area. The method determines a vessel diameter, a real-time location and measurements of the bubble cloud, and estimates a dwell position and dwell time. A dynamic displayed image that is indicative of a progression of the laser catheter treatment is presented, and commands may be generated to modify the laser catheter parameters responsive to the estimated dwell position, the estimated dwell time, and a recommended treatment protocol.

20 Claims, 3 Drawing Sheets

(51) Int. Cl.
     *A61B 18/00*          (2006.01)
     *A61B 18/24*          (2006.01)

(58) Field of Classification Search
     CPC .... A61B 2018/00642; A61B 2090/378; A61B
              18/245; A61B 5/0095; A61B 2018/0066;
              A61B 2018/00785; A61B 2018/00904
     See application file for complete search history.

(56)                References Cited

U.S. PATENT DOCUMENTS

| 2009/0227997 | A1  | 9/2009  | Wang   |            |
|--------------|-----|---------|--------|------------|
| 2010/0168571 | A1  | 7/2010  | Savery |            |
| 2012/0302877 | A1* | 11/2012 | Harks  | A61B 18/04 |
|              |     |         |        | 600/424    |

OTHER PUBLICATIONS

Tzou, et al: "Ultrasound guided morcellation during difficult Holmium laser enucleation of the prostate", David T T et al., pp. 171-172, Elsevier, 2019.

* cited by examiner

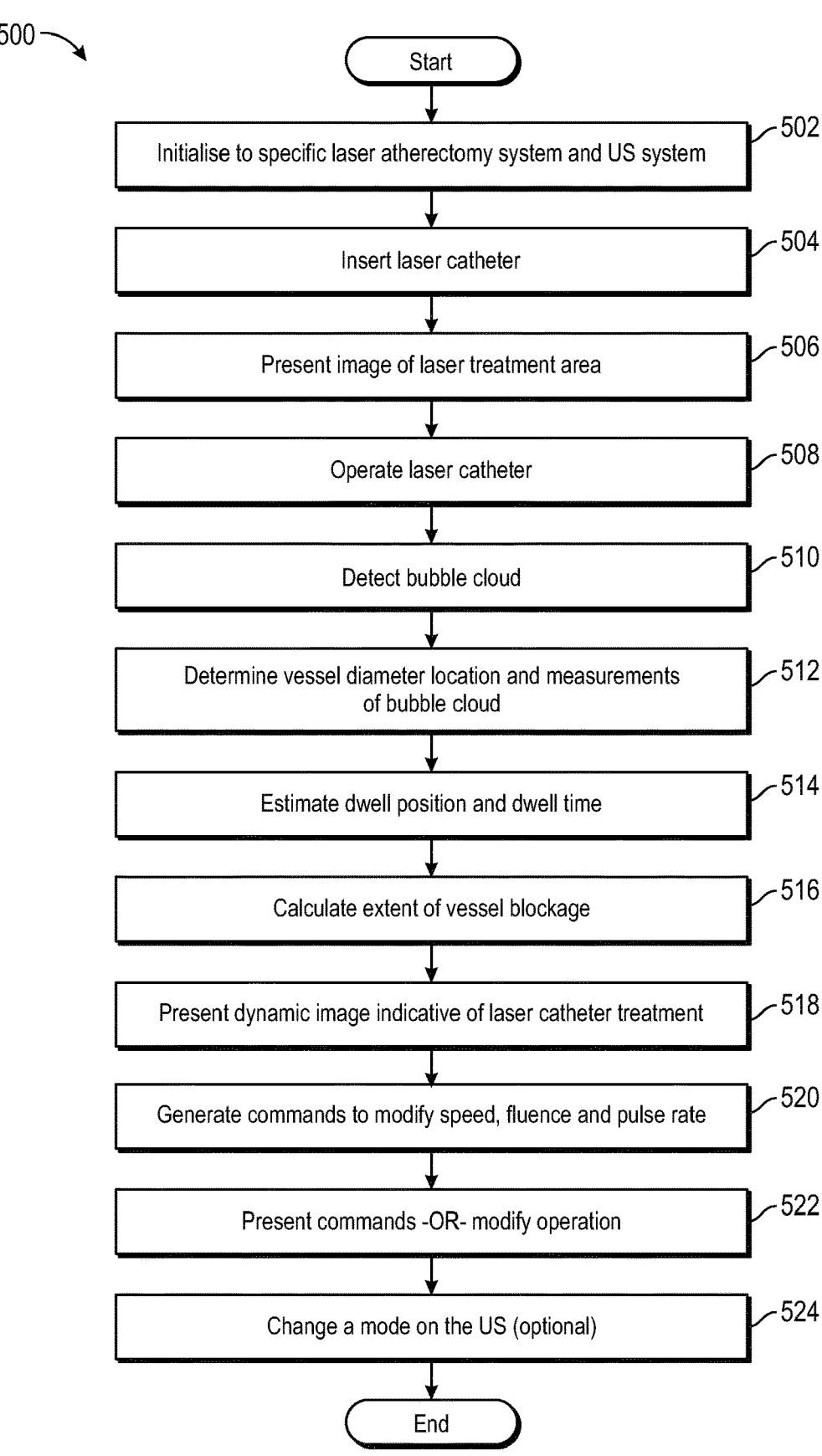

500

Start

Initialise to specific laser atherectomy system and US system — 502

Insert laser catheter — 504

Present image of laser treatment area — 506

Operate laser catheter — 508

Detect bubble cloud — 510

Determine vessel diameter location and measurements of bubble cloud — 512

Estimate dwell position and dwell time — 514

Calculate extent of vessel blockage — 516

Present dynamic image indicative of laser catheter treatment — 518

Generate commands to modify speed, fluence and pulse rate — 520

Present commands -OR- modify operation — 522

Change a mode on the US (optional) — 524

End

FIG. 5

SYSTEMS AND METHODS FOR LASER CATHETER TREATMENT IN A VESSEL LUMEN

CROSS REFERENCE TO RELATED APPLICATIONS

This application is the U.S. National Phase application under 35 U.S.C. § 371 of International Application No. PCT/EP2021/066741 filed Jun. 21, 2021, which claims the benefit of U.S. Provisional Patent Application No. 63/045,868 filed Jun. 30, 2020. These applications are hereby incorporated by reference herein.

TECHNICAL FIELD

The technical field generally relates to endovascular procedures, and more particularly relates to systems and methods for laser catheter treatment in a vessel lumen.

BACKGROUND

Endovascular procedures often use a therapy device, such as a catheter, in a vessel lumen to get rid of a blockage from a clot or plaque and to open the vessel lumen. To optimally treat the vessel, the therapy device must be activated and moved along a treatment area with an optimal amount of time at one or more optimal locations. In the case of laser atherectomy, when the laser from a laser catheter is turned on or activated, laser light essentially drills a hole in the clot/plaque thereby making a passage in the vessel lumen.

A technical problem is presented in controlling the laser catheter. If the laser catheter is not moved away from a location fast enough, it is described as having a dwell time that is too long, and there is a risk that the area may be over-treated. If the laser catheter is moved away from a location too quickly, it is described as having a dwell time that is too short, and the area may be under-treated, thus not meeting a desired treatment. Additionally, each laser catheter may have its own set of specifications for speed and activation time.

Currently, the vast majority of laser atherectomy procedures are performed under X-ray guidance. Unfortunately, without contrast (which is often not used), X-ray provides very limited information about the vessel anatomy or laser catheter efficacy.

Accordingly, technologically improved systems and methods for laser catheter treatment in a vessel lumen are desirable. The following disclosure provides these technological enhancements, in addition to addressing related issues.

BRIEF SUMMARY

This summary is provided to describe select concepts in a simplified form that are further described in the Detailed Description. This summary is not intended to identify key or essential features of the claimed subject matter, nor is it intended to be used as an aid in determining the scope of the claimed subject matter.

In one exemplary embodiment, a method for laser catheter treatment in a vessel lumen is provided. The method includes: inserting the laser catheter within the vessel lumen to a location of a treatment area, the laser catheter having a distal tip that outputs laser light; presenting an image of the treatment area within the vessel lumen based on using an ultrasound (US) imaging system; operating the laser catheter in the treatment area, wherein operating comprises moving the laser catheter at a prescribed speed and controlling a fluence and a pulse rate of the laser light; detecting, in real-time, a bubble cloud extending from the distal tip that is a function of the laser catheter operation in the treatment area using the US imaging transducer; determining a vessel diameter and a real-time location and measurements of the bubble cloud; estimating a laser catheter dwell position and dwell time as a function of the real-time location and the measurements of the bubble cloud; calculating a real-time extent of vessel blockage as a function of the real-time location and the measurements of the bubble cloud; presenting a dynamic displayed image of the vessel lumen and laser catheter operation that is indicative of a progression of the laser catheter treatment; and generating commands to modify the laser catheter parameters responsive to the estimated dwell position, the estimated dwell time, and a recommended treatment protocol.

Also, in one embodiment, the method includes, responsive to generating the commands, presenting the commands as alphanumeric messages for an operator to view, or automatically modifying parameters of the laser catheter.

Also, in one embodiment, the method includes changing an US system setting to an imaging mode responsive to activation of the laser system.

Also, in one embodiment, detecting the bubble cloud includes detecting sonic reflections in tissue media that are generated by an interaction of the laser light and anatomy of the vessel.

Also, in one embodiment, the method includes: determining a location of the bubble cloud includes determining an origin proximal the output of the laser light and an extent that is farthest from the output of the laser light; determining measurements of the bubble cloud includes identifying subsections that have different diameters and, for each subsection, storing the location, extent, and respective diameter; and further comprising periodically storing the location of the bubble cloud and the measurements of the bubble cloud.

Also, in one embodiment, the method includes: comparing a real-time location of the bubble cloud and measurement of the bubble cloud with a stored location of the bubble cloud and the measurement of the bubble cloud to determine a location change or a measurement change; and calculating the real-time extent of vessel blockage as a function of the location change or the measurement change.

Also, in one embodiment, the real-time extent of vessel blockage is presented as a percent of a vessel diameter.

Also, in one embodiment, the method includes moving the laser catheter at a prescribed speed includes moving the distal end of the catheter longitudinally from a point prior to the treatment area to a point near an end of the treatment area.

In another exemplary embodiment, a system for laser catheter treatment in a vessel lumen is provided. The system includes: a laser catheter having a distal tip that outputs laser light, the laser catheter having operating parameters of a prescribed speed, a fluence, and a pulse rate; an ultrasound (US) system configured to detect a bubble cloud associated with operation of the laser catheter in a treatment area within the vessel lumen, and generate US signals based thereon; a control system operationally coupled to the laser catheter and US system, the control system programmed to: receive the US signals; determine a vessel diameter and a real-time location and measurements of the bubble cloud based on the US signals; estimate a laser catheter dwell position and associated dwell time as a function of the real-time location and the measurements of the bubble cloud; present, on a display system, a dynamic displayed image of the vessel lumen and laser catheter operation; generate commands to modify the laser catheter parameters responsive to the estimated dwell position, the estimated dwell time, and a recommended treatment protocol; and responsive to generating the commands, present the commands as alphanumeric messages on the display system for an operator to view, or automatically modify parameters of the laser catheter.

Also, in an embodiment, the control system is further programmed to detect sonic reflections in tissue media that are generated by an interaction of the laser light and anatomy of the vessel.

Also, in an embodiment, the control system is further programmed to: determine a location of the bubble cloud by determining an origin 34 proximal the output of the laser light 11 and an extent 38 that is farthest from the output of the laser light; determine measurements of the bubble cloud by identifying subsections that have different diameters and, for each subsection, storing the location, extent, and respective diameter; and periodically store the location of the bubble cloud and the measurements of the bubble cloud.

Also, in an embodiment, the control system is further programmed to: compare a real-time location of the bubble cloud and measurement of the bubble cloud with a stored location of the bubble cloud and the measurement of the bubble cloud to determine a location change or a measurement change; and calculate the real-time extent of vessel blockage as a function of the location change or the measurement change.

Also, in an embodiment, the control system is further programmed to calculate a real-time extent of vessel blockage and present it on the display system.

Also, in an embodiment, the control system is further programmed to present the real-time extent of vessel blockage as a percent of a vessel diameter on the display system.

Also, in an embodiment, the control system is further programmed to estimate the dwell speed and the dwell time based on detected movement of the distal end of the catheter in the treatment area.

Also, in an embodiment, the control system is further programmed to change an US system setting responsive to an operation of the laser system.

In another exemplary embodiment, a system for laser catheter treatment in a vessel lumen is provided. The system includes: a laser atherectomy system having configurable operating parameters of a prescribed speed, a fluence, and a pulse rate that control an associated laser catheter that outputs laser light from a distal tip; an ultrasound (US) system configured to detect a bubble cloud of carbon dioxide or carbon monoxide generated by an interaction of the laser light and anatomy of the vessel in a treatment area within the vessel lumen, and generate US signals based thereon; a display system configured to present a dynamic displayed image of the vessel lumen and laser catheter operation; and a control system 108 operationally coupled to the laser atherectomy system, the US system, and the display system, the control system configured by programming instructions on computer readable to: receive the US signals; determine a real-time location and measurements of the bubble cloud based on the US signals; estimate a laser catheter dwell position and associated dwell time as a function of the real-time location and the measurements of the bubble cloud; generate commands to modify the laser catheter parameters responsive to the estimated dwell position, the estimated dwell time, and a prescribed treatment protocol; and responsive to generating the commands, present the commands as alphanumeric messages on the display system for an operator to view, or automatically modify parameters of the laser catheter.

Also in an embodiment, the control system is further configured to: determine a location of the bubble cloud by determining an origin 34 proximal the output of the laser light and an extent that is farthest from the output of the laser light; identify subsections of the bubble cloud that have different shapes and, for each subsection, measure the location, extent, and respective diameter; and periodically store the location of the bubble cloud and the measurements of the subsections of the bubble cloud.

Also in an embodiment, the control system is further configured to: compare a real-time measurement of a subsection of the bubble cloud with a stored measurement of the subsection of the bubble cloud to determine a measurement change; and calculate a real-time extent of vessel blockage as a function of the measurement change.

Also in an embodiment, the control system is further programmed to change an US system mode setting responsive to activating the laser system.

Furthermore, other desirable features and characteristics of the system and method will become apparent from the subsequent detailed description and the appended claims, taken in conjunction with the accompanying drawings and the preceding background.

BRIEF DESCRIPTION OF THE DRAWINGS

The present application will hereinafter be described in conjunction with the following drawing figures, wherein like numerals denote like elements, and:

FIG. 5 is a flow chart for a method system for a laser catheter treatment in a vessel lumen, in accordance with an exemplary embodiment.

DETAILED DESCRIPTION

Figure 1:
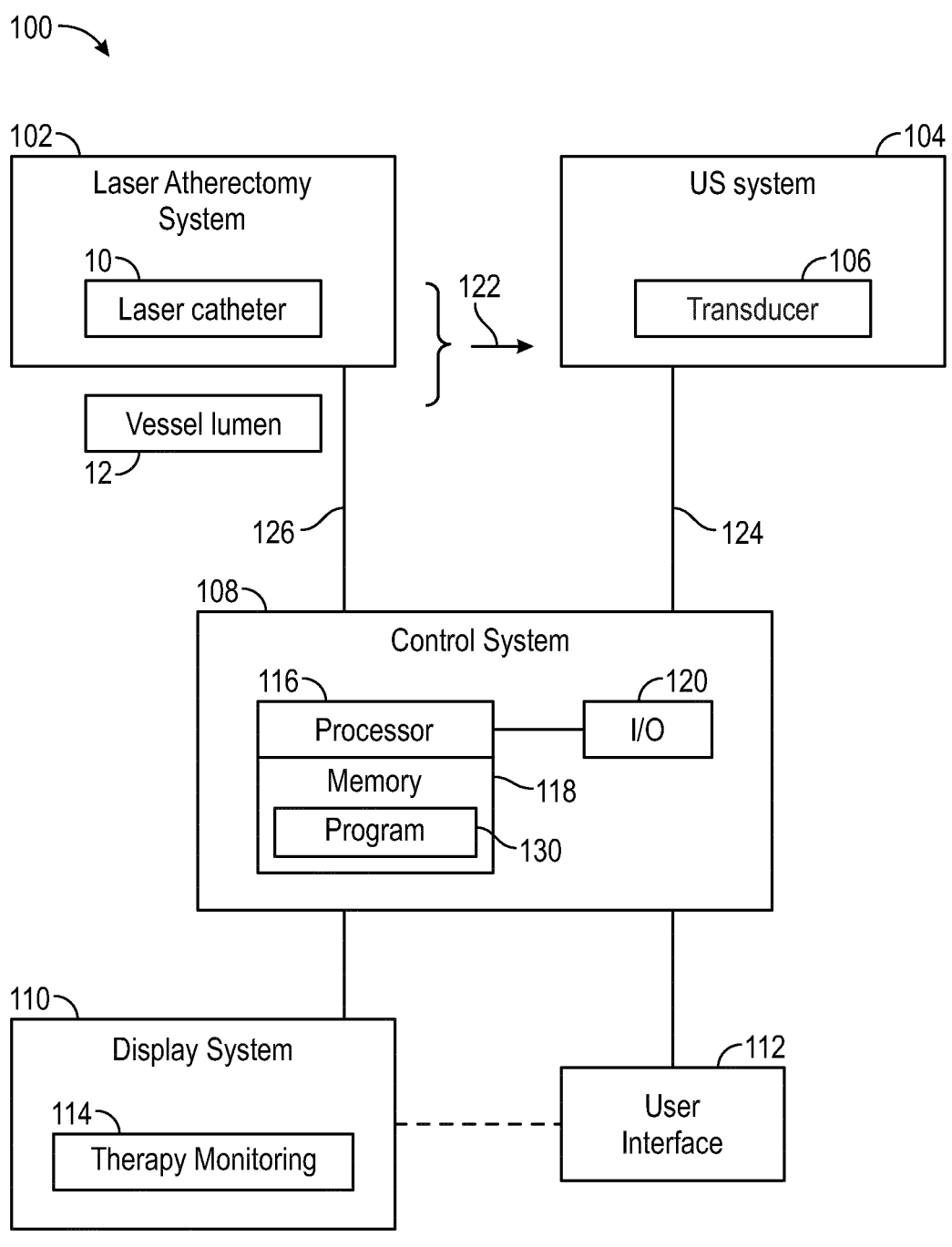
FIG. 1 is a block diagram of a system for laser catheter treatment in a vessel lumen, in accordance with an exemplary embodiment.

The following detailed description is merely illustrative in nature and is not intended to limit the embodiments of the subject matter or the application and uses of such embodiments. As used herein, the word "exemplary" means "serving as an example, instance, or illustration." Thus, any embodiment described herein as "exemplary" is not necessarily to be construed as preferred or advantageous over other embodiments. The embodiments described herein are exemplary embodiments provided to enable persons skilled in the art to make or use the invention and not to limit the scope of the invention that is defined by the claims. Furthermore, there is no intention to be bound by any expressed or implied theory presented in the preceding technical field, background, summary, or the following detailed description.

As mentioned, a technical problem is presented in controlling the laser catheter. If the laser catheter is not moved away from a location fast enough, it is described as having a dwell time that is too long, and there is a risk that the area may be over-treated. If the laser catheter is moved away from a location too quickly, it is described as having a dwell time that is too short, and the area may be under-treated, thus not meeting a desired treatment. Additionally, each laser catheter or catheter may have its own set of specifications for speed and activation time.

Currently, the vast majority of laser atherectomy procedures are performed under X-ray guidance. Unfortunately, without contrast (which is often not used), X-ray provides very limited information about the vessel anatomy. This lack of information results in a number of challenges for clinicians:

Visualizing the vessel wall during treatment: since soft tissue is not visible under X-ray, clinicians are only able to see the device in 2D during the treatment. Instead, they have to remember where they have treated, and for how long the device was activated in each location. This requires building up a mental map of the therapy, which requires a lot of experience.

It is difficult to do a contrast run during treatment, since this would require removing or displacing the laser catheter from the treatment area. Thus, the only confirmation of treatment occurs after the procedure.

Similarly, it is difficult to see lesions and plaque under X-ray. Lesions are often missed, even with contrast, resulting in under-treatment and high rates of restenosis.

It can be very difficult for the physician to follow the prescribed speeds and activation times and therefore portions of the vessel may be over-treated or under-treated.

Tortuous vessels that are only visualized with 2D X-ray images can result in suboptimal treatment. This can result in under treatment because the physician may quickly navigate the catheter past the bend without realizing the presence of disease at the bend.

Complications during atherectomy, such as vessel damage and dissection, are difficult or impossible to detect under X-ray alone.

Some solutions have attempted to use an ultrasound (US) imaging system, but have encountered problems due to variations in quality of vessel/anatomy visualization and can also vary depending on a number of factors such as intervening tissue, fat percentage, thickness of sub-cutaneous fat layer etc.

Exemplary embodiments provide a technical solution to this problem in the form of a control system (FIG. 1 108) embodying novel rules, vascular anatomy design factors and recommended treatment protocols for combining laser catheter treatment using laser atherectomy systems and methods and ultrasound (US) imaging, as follows.

Laser atherectomy systems and methods for laser catheter treatment in a vessel lumen employ laser energy from a laser catheter. When the laser energy is activated in a vessel, a large water vapor bubble cloud is formed at the catheter distal tip as the low-pressure state vaporizes surrounding water. The tunable operating parameters in a laser atherectomy system are pulse rate and pulse intensity. The lifetime of a bubble cloud can be from 50 us to 300 us, while the diameter may be up to 3 mm. The size of the bubble cloud is essentially related to the energy level (higher energy creates a larger bubble). Upon cavitation, it breaks apart into smaller bubbles and persists downstream, or aft from its origin. These downstream bubble clouds are gaseous products from the photochemical reaction with blood/tissues/contrast. Concentration of hemoglobin affects bubble cloud size. Laser activation in contrast media yields large amounts of carbon monoxide (CO) and carbon dioxide ($CO_2$).

Ultrasound (US) images are based on sonic reflections from tissue media. Reflections from the above described bubbles produced during laser activation are strong and therefore show up bright on the US images. Provided embodiments detect and measure the bubble cloud on the ultrasound (US) images.

The disclosed control system 108 forms a closed loop control between a laser atherectomy system (with associated laser catheter), and an ultrasound (US) imaging system configured to detect a gas bubble cloud resulting from operation of the laser catheter. The vascular anatomy design factors and recommended treatment protocols include thresholds to identify and measure these gas bubble clouds in vessel lumens and in various types of treatment areas. The disclosed control system 108 further generates commands and presents images for therapy monitoring on a display system and receives user input from a user interface.

Provided embodiments provide an improved human-machine interface, a display for real-time assessment of the laser catheter efficacy under ultrasound (US). The technological improvement includes feedback loops to the physician and/or laser atherectomy system to guide the laser catheter for optimal treatment. Provided embodiments aid in therapy monitoring based on acquiring, processing, and visualizing ultrasound images of gas bubbles generated by the laser's interaction with tissue during treatment. Bi-directional communication between the laser atherectomy system and US systems, via a controller system, enable automated US system mode transition, automated calculation of therapy dwell times, and automated adjustment of imaging and laser delivery parameters (fluence and pulse rate) based on real-time processing of ultrasound images. The figures and descriptions below provide more detail.

Turning now to FIG. 1, in an embodiment, the system for a laser catheter treatment in a vessel lumen 100 (also referred to herein as "system" 100) is depicted as associated with a vessel lumen 12. In various embodiments, the vessel lumen 12 is a blood vessel in a patient. As mentioned, the system 100 embodies the control system 108, which is operationally coupled to the laser atherectomy system 102 via bidirectional connection 126, and to the US system 104 via bidirectional connection 124. Connection 124 and connection 126 may each comprise, without limitation, direct hard-wired connections, fiber optics, infrared and/or wireless bus technologies. In various embodiments, the control system 108 is also operationally coupled to a display system 110 and a user interface 112. Although the control system 108 is depicted as an individual functional block for the purpose of discussion, it may be appreciated that, in some embodiments, the control system 108 may be integrated within any combination of an existing laser atherectomy system 102, display system 110, and user interface 112; in other embodiments, the control system 108 may be integrated within any combination of an existing US system 104, display system 110, and user interface 112. The functions of these systems, and their interaction, are described in more detail below.

Figure 2:
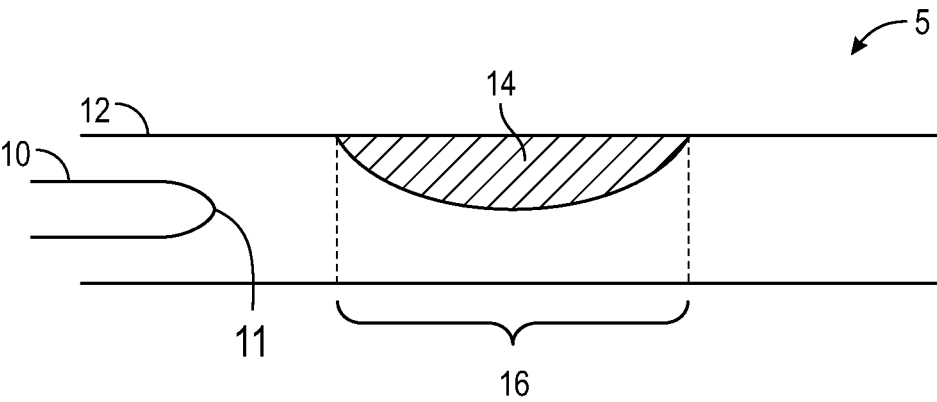
FIGS. 2-4 illustrate simplified screen shots from a dynamic progression of US images that may be generated during a laser catheter treatment in a treatment area of a vessel lumen, in accordance with an embodiment.
Figure 3:
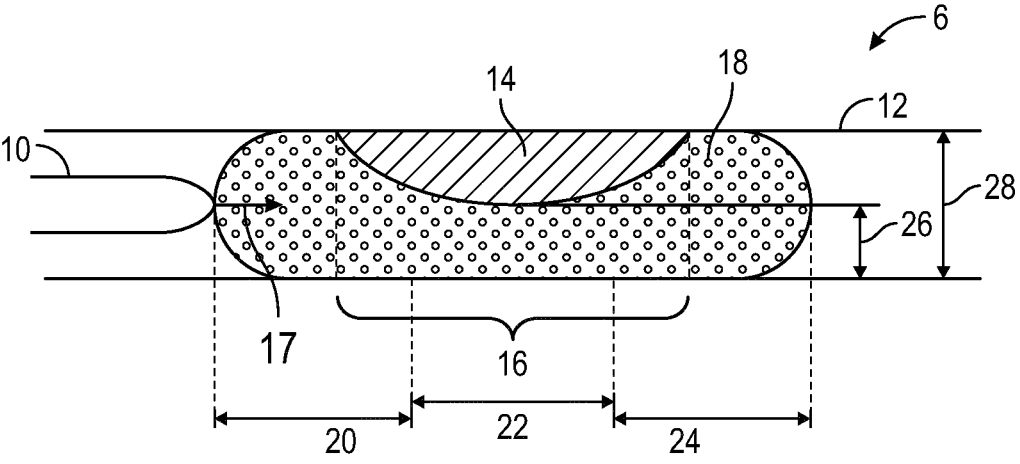

The laser atherectomy system 102 includes a laser catheter 10 that emits a laser light (FIG. 3, 17). The laser catheter 10 may be manually operated by a user; manual input can include a speed, a dwell time, and a direction. The direction is generally, from the perspective of the distal tip of the laser catheter, forward and aft, longitudinally, within a vessel lumen (FIG. 2, 12). The laser atherectomy system 102 controls a fluence of the laser light 17 and a pulse rate of the laser light 17, generally in response to user input. User input may be provided via user interface 112 and/or a combination of the user input and user selected predefined treatment protocols. Operating the laser catheter (10) in a treatment area (FIG. 2 16), comprises moving the laser catheter (10) at a prescribed speed and controlling the laser catheter parameters, such as the fluence and the pulse rate of the laser light (17). In various embodiments, as described in more detail below, the control system 108 may automatically modify the laser catheter parameters.

The US system 104 employs an ultrasound transducer 106 and supporting circuitry to detect information at 122 (from the vessel lumen 12 and surrounding anatomy) and convert detected information into US signals transmitted via connection 124 for further processing by the control system 108 and for display on the display system 110. As used herein, the detected information at 122 is in the form of a bubble cloud and detecting the bubble cloud includes detecting carbon dioxide and/or carbon monoxide that are each generated by an interaction of the laser light 17 and anatomy of the vessel. Input to the US system 104 from the control system 108 may include US system settings, such as, zoom, contrast, and repositioning of images.

The user interface 112 and the control system 108 are cooperatively configured to allow a user to interact with display devices in the display system 110 and/or other elements of the system 100, as described herein. Depending on the embodiment, the user interface 112 may be realized as a cursor control device (CCD), keypad, touchpad, keyboard, mouse, touch panel (or touchscreen), joystick, knob, line select key, voice controller, gesture controller, or another suitable device adapted to receive input from a user. When the user interface 112 is configured as a touchpad or touchscreen, it may be integrated with the display system 110.

The control system 108 generates display commands for the display system 110 to present thereon an image for use in therapy monitoring. The image may comprise pictorial images plus any of various alphanumeric messages, graphical user interface elements, tables, icons, alerts, menus, and buttons, as described herein. The display system 110 is configured to continuously receive and process the display commands from the control system 108. In various embodiments described herein, the display system 110 may present two- or three-dimensional images and may be realized on one or more electronic display devices cooperatively configured. Renderings on the display system 110 may be processed by a graphics system, components of which may be integrated into the display system 110 and/or be integrated within the control system 108. Display methods also include various formatting techniques for visually distinguishing objects from among other similar objects.

The control system 108 performs the functions of the system 100. As used herein, the control system 108 refers to any means for facilitating communications and/or interaction between the elements of the system 100 and performing additional processes, tasks and/or functions to support operation of the system 100, as described herein. In various embodiments, the control system 108 may be any hardware, software, firmware, electronic control component, processing logic, and/or processor device, individually or in any combination. Depending on the embodiment, the control system 108 may be implemented or realized with a general purpose processor (shared, dedicated, or group) controller, microprocessor, or microcontroller, and memory that executes one or more software or firmware programs; a content addressable memory; a digital signal processor; an application specific integrated circuit (ASIC), a field programmable gate array (FPGA); any suitable programmable logic device; combinational logic circuit including discrete gates or transistor logic; discrete hardware components and memory devices; and/or any combination thereof, designed to perform the functions described herein.

Accordingly, in FIG. 1, an embodiment of the control system 108 is depicted as an enhanced computer system including a processor 116 and a computer readable media, memory 118. Generally, the memory 118 maintains data bits and may be utilized by the processor 116 as storage and/or a scratch pad during operation. Information in the memory 118 may be organized and/or imported from an external data source during an initialization step of a process or method; it may also be programmed via a user interface 112. In the embodiment of FIG. 1, the memory 118 stores instructions and applications, including a novel program 130 with rules and programming instructions which, when executed, convert the processor 116/memory 118 configuration into the control system 108, which performs the functions, techniques, and processing tasks associated with the operation of the system 100.

In various embodiments, the processor/memory unit of the control system 108 may be communicatively coupled to an input/output (I/O) interface 120. The I/O interface 120 enables intra control system 108 communication, as well as communications between the control system 108 and other system 100 components. The I/O interface 120 may include one or more network interfaces and can be implemented using any suitable method and apparatus. In various embodiments, the I/O interface 120 is configured to support communication from an external system driver and/or another computer system. In one embodiment, the I/O interface 120 obtains data from external data source(s) directly. Also, in various embodiments, the I/O interface 120 may support communication with technicians, and/or one or more storage interfaces for direct connection to storage apparatuses.

Those skilled in the art will recognize that the mechanisms of the present disclosure are capable of being distributed as a program product. As a program product, one or more types of non-transitory computer-readable signal bearing media may be used to store and distribute the program 130, such as a non-transitory computer readable medium bearing the program 130 and containing therein additional computer instructions for causing a computer processor (such as the processor 116) to load and execute the program 130. Such a program product may take a variety of forms, and the present disclosure applies equally regardless of the type of computer-readable signal bearing media used to carry out the distribution. Examples of signal bearing media include recordable media such as floppy disks, hard drives, memory cards and optical disks, and transmission media such as digital and analog communication links. It will be appreciated that cloud-based storage and/or other techniques may also be utilized in certain embodiments.

Figure 4:
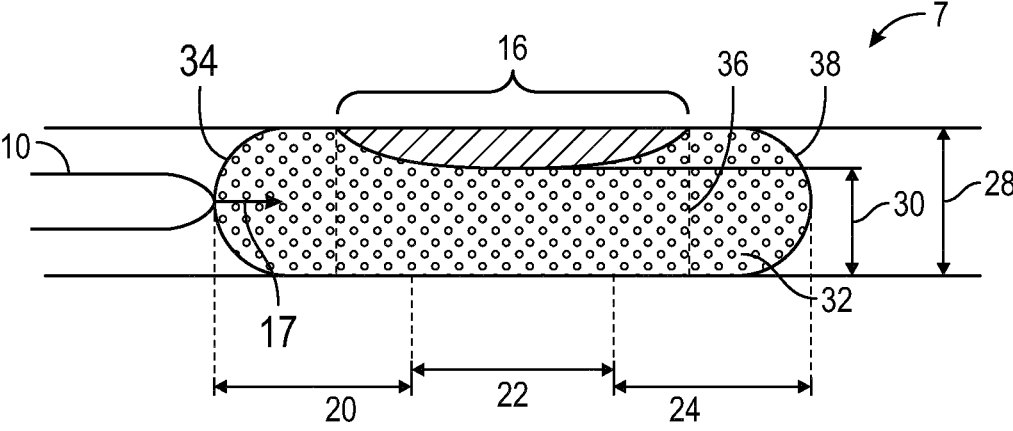

Turning now to FIGS. 2-4, images 5-7 provide non-limiting examples for describing technological enhancements over other laser catheter treatment systems. The images 5-7 of FIGS. 2, 3, and 4 illustrate simplified screen shots from a dynamic progression of US images that are generated during a laser catheter treatment in a treatment area 16 of a vessel lumen 12, in accordance with an embodiment. The images of FIGS. 2, 3, and 4 are presented on the display system 110, responsive to the control system 108, and are understood to be responsive to continuously obtaining and processing data from the US system 104 and the laser atherectomy system 102. The images of FIGS. 2, 3, and 4 are illustrated as two dimensional, but in practice, the images may be three-dimensional. Regardless of whether the images displayed are two- or three-dimensional, it is understood that the vessel lumen anatomy and measurements of the bubble cloud 18 and vessel blockage 14 described herein are volumetric or three-dimensional.

Before operation of the system 100, the control system 108 is initialized to calibrate to the specific laser atherectomy system 102, specific laser catheter 10, and to the specific US system 104. The calibration enables the control system 108 to synchronize laser catheter 10 operation and parameter changes with expected laser light 17 output and with received US system 104 information. In an example, the control system 108 can have both the US system 104 and the laser atherectomy system 102 send a clock signal or time stamp and then align the two system clocks. In another example, the control system 108 can act as the trigger, sending a clock signal or time stamp to both the US system 104 and the laser atherectomy system 102 so that they are activated simultaneously. Additionally, the activation of the laser atherectomy system 102 could trigger automatic transition of the US system 104 to specific imaging modes, such as contrast mode or other customized mode that is optimized to visualize the gas bubbles to monitor the therapy.

The laser catheter (10) is operated in the treatment area (16), wherein operating comprises moving the laser catheter at a prescribed speed and controlling laser catheter parameters including a fluence and a pulse rate of the laser light (17). The prescribed speed may be a distance per time, over the course of a treatment area 16 length, perhaps with some margin. For example, with reference to FIG. 4, the laser catheter 10 may be moved such that the distal end 11 is moved within the treatment area 16, between point 34 before the start of the treatment area to point 36 near the end of the treatment area (in FIG. 4, before the start of the treatment area 16 is on the left, near where the distal end 11 would initially be inserted, and the end of the treatment area 16 is on the right). The laser catheter 10 may be moved forward and aft in this treatment area 16 more than once. Operation of the laser catheter 10 results in generation of carbon dioxide and carbon monoxide that are each generated by an interaction of the laser light 17 and anatomy of the vessel. The US system 104 detects in real-time, a bubble cloud (18) extending from the distal tip (11) that is a function of the laser catheter operation in the treatment area 16 using the US ultrasound transducer 106.

The control system 108 processes information received from the US system 104 and uses hyperechoic visualization and rules encoded into the program 130 to determine a vessel diameter (28) and a real-time location and volumetric measurements of the bubble cloud. Using the detected bubble cloud determinations, the control system 108 may estimate movement of the distal end 11 of the laser catheter in the treatment area 16, and corresponding dwell speed and dwell time.

Determining a location of the bubble cloud includes determining an origin at point 34 proximal the output of the laser light 11 and an extent 38 that is farthest from the output of the laser light. Determining measurements of the bubble cloud includes identifying subsections (20, 22, 24) that have different shapes and diameters and, for each subsection, storing the location, extent, and respective diameter. The control system 108 may compare a real-time measurement of a subsection of the bubble cloud with a stored measurement of the subsection of the bubble cloud to determine a measurement change; and calculate a real-time extent of vessel blockage 14 as a function of the measurement change. The control system 108 may also periodically store the location of the bubble cloud and the measurements of the bubble cloud.

In the provided examples, the bubble cloud appears bone-shaped and volumetric measurements (20, 22, 24, 26, 28, 30) of the bubble cloud include measurements of the subsections: a round subsection (length 20) proximate the distal tip 11 of the catheter 10; a narrow subsection (length 22) in the area of the thickest vessel blockage (vessel blockage 14 is shown to reduce throughput to a diameter 26 at the thickest region, out of a total vessel diameter of 28); and returning to a round subsection (length 24) and diameter 28. It may be appreciated that other bubble cloud shapes may be generated, and that, for each bubble shape, the system 100 will utilize rules encoded into the program 130 to segment the bubble shape into subsections and determine the measurements in a similar process as described here. The control system 108 may calculate a real-time extent of vessel blockage (14) as a function of the real-time location and the measurements of the bubble cloud.

The control system 108 may also perform temporal analysis by estimating the bulk velocity of bubbles throughout the bubble cloud. Due to known principles of energy decay over time, the bubbles at the catheter distal tip 11 can be expected to have the highest velocity, and bubbles farther from the tip would travel more slowly. In various embodiments, the bubble velocity information could be combined with the estimated dwell position of the device, thereby improving accuracy of distal tip 11 detection compared to using either modality alone. This could for example help during extended periods of therapy where the treatment area gets flooded with bubbles; in this case the vessel lumen is completely hyperechoic due to saturation with bubbles and the laser catheter 10 and many occlusions should present as hyperechoic structures, but the laser catheter distal tip 11 is the only moving hyperechoic structure.

The control system 108 presents a dynamic displayed image for use in therapy monitoring (for example, images 5, 6, 7 are indicative of a progression of the laser catheter treatment). The control system 108 estimates the above mentioned dwell position (e.g., from point 34 to point 36) and an associated dwell time for various dwell positions as a function of the real-time location and the measurements of the bubble cloud 18. As used herein, dwell time is an amount of time spent by the activated laser light 17 at a given dwell location; and, the dwell location may be varied from a starting point to an ending point (such as point 34 to point 36, with the area between point 36 and bubble boundary 38 representing the extent of the bubble cloud emanating from the distal tip 11 when the distal tip 11 is at location 36 and generating laser light 17 therefrom). These estimations may be presented on the display system 110 for therapy monitoring.

Bubble cloud shape and measurements can be used by the control system 108 to measure and present treatment progress in therapy monitoring. In various embodiments, the control system 108 compares a real-time location of the bubble cloud and measurement of the bubble cloud with a stored location of the bubble cloud and stored measurement of the bubble cloud to determine a location change or a measurement change; the control system 108 can calculate the real-time extent of vessel blockage 14 as a function of the location change or the measurement change. In various embodiments, the real-time extent of vessel blockage 14 is presented as a percent of a vessel diameter 28.

In FIG. 4, after at least some treatment has been performed, the resulting area of the thickest vessel blockage 14 is shown reduced, i.e., the throughput in the treatment area has been increased to a diameter of 30 at the thickest region, out of the total vessel diameter of 28. As depicted, diameter 30 is smaller than diameter 28 but is larger than the pre-treatment diameter 26.

In various embodiments, the control system 108 generates commands to modify the laser catheter parameters responsive to the estimated dwell position, the estimated dwell time, and a recommended treatment protocol. In various embodiments, responsive to generating the commands, the control system 108 presents the commands as alphanumeric messages for an operator to view. In various embodiments, responsive to generating the commands, the control system 108 automatically modifies parameters of the laser catheter. In various embodiments, the control system 108 changes an US system 104 setting responsive to an operation of the laser catheter.

In operation, any of the following features may be provided by the control system 108, based on the measurements it takes, processes and stores. The control system 108 may identify gaps in anatomy where dwell time was insufficient and/or anticipate a potential over-treatment and generate respective alphanumeric warnings and guidance. The feedback can be used by a practitioner to maintain as consistent as possible of a dwell time map throughout the vessels. The control system 108 may constantly modulate the power (fluence)/pulse rate as a function of the dwell times and velocity of the catheter as it is being pushed.

The system 100 may make its determinations and selections in accordance with a method such as method 500 of FIG. 5. With continued reference to FIGS. 1-4, a flow chart is provided for a method 500 for providing a system 100, in accordance with various exemplary embodiments. Method 500 represents various embodiments of a method for selecting an accurate runway record. For illustrative purposes, the following description of method 500 may refer to elements mentioned above in connection with FIG. 1. In practice, portions of method 500 may be performed by different components of the described system. It should be appreciated that method 500 may include any number of additional or alternative tasks, the tasks shown in FIG. 5 need not be performed in the illustrated order, and method 500 may be incorporated into a more comprehensive procedure or method having additional functionality not described in detail herein. Moreover, one or more of the tasks shown in FIG. 5 could be omitted from an embodiment of the method 500 if the intended overall functionality remains intact.

The method starts, and at 502 the control system 108 is initialized and the system 100 is in operation. Initialization may comprise uploading or updating an algorithm embodied in program 130, various lookup tables, such as the prescribed treatment protocols, various laser catheter specific operational guidelines, default parameters, predetermined dwell times and distance thresholds, and the various shapes, various colors and/or visually distinguishing techniques used for icons and alphanumeric displays. In some embodiments, program 130 includes additional instructions and rules for rendering information differently based on type of US system 104 and/or type of display device in display system 110.

At 504, the method includes inserting the laser catheter 10 within the vessel lumen to a location of a treatment area 16, the laser catheter having a distal tip 11 that outputs laser light 17. At 506, the method includes presenting an image of the treatment area within the vessel lumen based on using an ultrasound (US) imaging system 104. Operating the laser catheter 10 in the treatment area 16 is at 508, wherein operating comprises moving the laser catheter at a prescribed speed and controlling a fluence and a pulse rate of the laser light 17.

At 510 a bubble cloud 18 extending from the distal tip 11 that is a function of the laser catheter operation in the treatment area using the US imaging transducer is detected, in real-time. A vessel diameter 28 and a real-time location and measurements of the bubble cloud 18 are determined at 512. At 514, the method includes estimating a laser catheter dwell position (e.g., from point 34 to point 36) and dwell time as a function of the real-time location and the measurements of the bubble cloud. The method may calculate a real-time extent of vessel blockage 14 as a function of the real-time location and the measurements of the bubble cloud at 516. At 518, the method includes presenting a dynamic displayed image (5, 6, 7) of the vessel lumen and laser catheter operation that is indicative of a progression of the laser catheter treatment. The method includes generating commands to modify the laser catheter parameters responsive to the estimated dwell position, the estimated dwell time, and a recommended treatment protocol at 520. In some embodiments, at 522, the method includes, responsive to generating the commands, presenting the commands as alphanumeric messages for an operator to view. In other embodiments, at 522, the method includes, responsive to generating the commands, automatically modifying parameters of the laser catheter 10.

In an example, a guideline for atherectomy stored as a prescribed treatment may suggest that an optimal speed to advance the laser catheter 10 is in the range of 1-2 mm/sec. The estimated dwell speed could be used to provide a speed indicator on the display system 110 to the user and guidance on whether to speed up or slow down. For example, if the control system 108 determines that the catheter is positioned against a vascular blockage such as a piece of plaque, the indicator would suggest for the speed to decrease and more time to be spent around the plaque. On the other hand, if the control system 108 determines that the catheter is passing through healthy vessel, then the recommendation would be to speed up.

At 524 the method may optionally change an US system 104 setting responsive to an operation of the laser catheter 10.

Thus, a technologically enhanced system 100 for laser catheter treatment with an improved human-machine interface is provided. The provided system 100 embodies a control system 108, that draws upon data and information from the US system 104 and from the laser atherectomy system 102 to present a dynamic displayed image (5, 6, 7) of the vessel lumen 12 and laser catheter 10 operation that is indicative of a progression of the laser catheter treatment. As is readily appreciated, the above examples of the system 100 are non-limiting, and many others may be addressed by the control system 108.

Those of skill in the art will appreciate that the various illustrative logical blocks, modules, circuits, and algorithm steps described in connection with the embodiments disclosed herein may be implemented as electronic hardware, computer software, or combinations of both. Some of the embodiments and implementations are described above in terms of functional and/or logical block components (or modules) and various processing steps. However, it should be appreciated that such block components (or modules) may be realized by any number of hardware, software, and/or firmware components configured to perform the specified functions. To clearly illustrate the interchangeability of hardware and software, various illustrative components, blocks, modules, circuits, and steps have been described above generally in terms of their functionality. Whether such functionality is implemented as hardware or software depends upon the application and design constraints imposed on the overall system.

Skilled artisans may implement the described functionality in varying ways for each application, but such implementation decisions should not be interpreted as causing a departure from the scope of the present invention. For example, an embodiment of a system or a component may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments described herein are merely exemplary implementations.

Further, the various illustrative logical blocks, modules, and circuits described in connection with the embodiments disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of the method or algorithm described in connection with the embodiments disclosed herein may be embodied directly in hardware, in a software module executed by a controller or processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC.

In this document, relational terms such as first and second, and the like may be used solely to distinguish one entity or action from another entity or action without necessarily requiring or implying any actual such relationship or order between such entities or actions. Numerical ordinals such as "first," "second," "third," etc. simply denote different singles of a plurality and do not imply any order or sequence unless specifically defined by the claim language. The sequence of the text in any of the claims does not imply that process steps must be performed in a temporal or logical order according to such sequence unless it is specifically defined by the language of the claim. When "or" is used herein, it is the logical or mathematical or, also called the "inclusive or." Accordingly, A or B is true for the three cases: A is true, B is true, and, A and B are true. In some cases, the exclusive "or" is constructed with "and;" for example, "one from the set A and B" is true for the two cases: A is true, and B is true.

Furthermore, depending on the context, words such as "connect" or "coupled to" used in describing a relationship between different elements do not imply that a direct physical connection must be made between these elements. For example, two elements may be connected to each other physically, electronically, logically, or in any other manner, through one or more additional elements.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A method for laser catheter treatment in a vessel lumen, comprising:
   inserting the laser catheter within the vessel lumen to a location of a treatment area, the laser catheter having a distal tip that outputs laser light;
   presenting an image of the treatment area within the vessel lumen based on using an ultrasound (US) imaging system;
   operating the laser catheter in the treatment area, wherein operating comprises moving the laser catheter at a prescribed speed and controlling a fluence and a pulse rate of the laser light;
   detecting, in real-time, a bubble cloud extending from the distal tip that is a function of the laser catheter operation in the treatment area using the US imaging transducer;
   determining a vessel diameter and a real-time location and measurements of the bubble cloud;
   estimating a laser catheter dwell position and dwell time as a function of the real-time location and the measurements of the bubble cloud;
   calculating a real-time extent of vessel blockage as a function of the real-time location and the measurements of the bubble cloud;
   presenting a dynamic displayed image of the vessel lumen and laser catheter operation that is indicative of a progression of the laser catheter treatment; and
   generating commands to modify the laser catheter parameters responsive to the estimated dwell position, the estimated dwell time, and a recommended treatment protocol.

2. The method of claim 1, further comprising, responsive to generating the commands, presenting the commands as alphanumeric messages for an operator to view, or automatically modifying parameters of the laser catheter.

3. The method of claim 2, further comprising changing an US system setting to an imaging mode responsive to activation of the laser system.

4. The method of claim 1, wherein detecting the bubble cloud includes detecting sonic reflections in tissue media from bubbles that are generated by an interaction of the laser light and anatomy of the vessel.

5. The method of claim 4, wherein:
   determining a location of the bubble cloud includes determining an origin proximal the output of the laser light and an extent that is farthest from the output of the laser light;
   determining measurements of the bubble cloud includes identifying subsections that have different diameters and, for each subsection, storing the location, extent, and respective diameter; and further comprising periodically storing the location of the bubble cloud and the measurements of the bubble cloud.

6. The method of claim 5, further comprising:

comparing a real-time location of the bubble cloud and measurement of the bubble cloud with a stored location of the bubble cloud and the measurement of the bubble cloud to determine a location change or a measurement change; and calculating the real-time extent of vessel blockage as a function of the location change or the measurement change.

7. The method of claim 5, wherein the real-time extent of vessel blockage is presented as a percent of a vessel diameter.

8. The method of claim 1, wherein moving the laser catheter at a prescribed speed includes moving the distal end of the catheter longitudinally from a point prior to the treatment area to a point near an end of the treatment area.

9. A system for laser catheter treatment in a vessel lumen, comprising:

a laser catheter having a distal tip that outputs laser light, the laser catheter having operating parameters of a prescribed speed, a fluence, and a pulse rate;

an ultrasound (US) system configured to detect a bubble cloud associated with operation of the laser catheter in a treatment area within the vessel lumen, and generate US signals based thereon;

a control system operationally coupled to the laser catheter and US system, the control system programmed to:

receive the US signals;

determine a vessel diameter and a real-time location and measurements of the bubble cloud based on the US signals;

estimate a laser catheter dwell position and associated dwell time as a function of the real-time location and the measurements of the bubble cloud;

present, on a display system, a dynamic displayed image of the vessel lumen and laser catheter operation;

generate commands to modify the laser catheter parameters responsive to the estimated dwell position, the estimated dwell time, and a recommended treatment protocol; and responsive to generating the commands, present the commands as alphanumeric messages on the display system for an operator to view, or automatically modify parameters of the laser catheter.

10. The system of claim 9, wherein the control system is further programmed to detect sonic reflections in tissue media from bubbles that are generated by an interaction of the laser light and anatomy of the vessel.

11. The system of claim 10, wherein the control system is further programmed to:

determine a location of the bubble cloud by determining an origin proximal the output of the laser light and an extent that is farthest from the output of the laser light;

determine measurements of the bubble cloud by identifying subsections that have different diameters and, for each subsection, storing the location, extent, and respective diameter; and periodically store the location of the bubble cloud and the measurements of the bubble cloud.

12. The system of claim 11, wherein the control system is further programmed to:

compare a real-time location of the bubble cloud and measurement of the bubble cloud with a stored location of the bubble cloud and the measurement of the bubble cloud to determine a location change or a measurement change; and calculate the real-time extent of vessel blockage as a function of the location change or the measurement change.

13. The system of claim 12, wherein the control system is further programmed to calculate a real-time extent of vessel blockage and present it on the display system.

14. The system of claim 13, wherein the control system is further programmed to present the real-time extent of vessel blockage as a percent of a vessel diameter on the display system.

15. The system of claim 12, wherein the control system is further programmed to estimate the dwell speed and the dwell time based on detected movement of the distal end of the catheter in the treatment area.

16. The system of claim 15, wherein the control system is further programmed to change an US system mode setting responsive to an operation of the laser system.

17. A system for laser catheter treatment in a vessel lumen, comprising:

a laser atherectomy system having configurable operating parameters of a prescribed speed, a fluence, and a pulse rate that control an associated laser catheter that outputs laser light from a distal tip;

an ultrasound (US) system configured to detect a bubble cloud of carbon dioxide or carbon monoxide generated by an interaction of the laser light and anatomy of the vessel in a treatment area within the vessel lumen, and generate US signals based thereon;

a display system configured to present a dynamic displayed image of the vessel lumen and laser catheter operation; and a control system operationally coupled to the laser atherectomy system, the US system, and the display system, the control system configured by programming instructions on computer readable to:

receive the US signals;

determine a real-time location and measurements of the bubble cloud based on the US signals;

estimate a laser catheter dwell position and associated dwell time as a function of the real-time location and the measurements of the bubble cloud;

generate commands to modify the laser catheter parameters responsive to the estimated dwell position, the estimated dwell time, and a prescribed treatment protocol; and responsive to generating the commands, present the commands as alphanumeric messages on the display system for an operator to view, or automatically modify parameters of the laser catheter.

18. The system of claim 17, wherein the control system is further configured to:

determine a location of the bubble cloud by determining an origin proximal the output of the laser light and an extent that is farthest from the output of the laser light;

identify subsections of the bubble cloud that have different shapes and, for each subsection, measure the location, extent, and respective diameter; and periodically store the location of the bubble cloud and the measurements of the subsections of the bubble cloud.

19. The system of claim 18, wherein the control system is further configured to:

compare a real-time measurement of a subsection of the bubble cloud with a stored measurement of the subsection of the bubble cloud to determine a measurement change; and calculate a real-time extent of vessel blockage as a function of the measurement change.

20. The system of claim 19, wherein the control system is further programmed to change an US system mode setting responsive to activating the laser system.

\* \* \* \* \*